(12) United States Patent
Macoviak et al.

(10) Patent No.: US 6,702,773 B1
(45) Date of Patent: Mar. 9, 2004

(54) METHODS AND DEVICES FOR PERFORMING DIFFERENTIAL PERFUSION

(75) Inventors: John Macoviak, La Jolla, CA (US); Brady Esch, San Jose, CA (US); Mike Lee, San Francisco, CA (US); Wilfred J. Samson, Saratoga, CA (US)

(73) Assignee: Cardeon Corporation, Cupertino, CA (US)

( * ) Notice: Subject to any disclaimer, the term of this patent is extended or adjusted under 35 U.S.C. 154(b) by 0 days.

(21) Appl. No.: 09/495,632

(22) Filed: Feb. 1, 2000

(51) Int. Cl.$^7$ ............................................. A61M 37/00
(52) U.S. Cl. ..................... 604/4.01; 604/6.11; 604/6.14
(58) Field of Search ................... 604/4.01, 5.01, 604/7, 8, 96.01, 113, 9, 6.11, 6.13, 6.14, 6.16, 131, 151; 422/44–48

(56) References Cited

U.S. PATENT DOCUMENTS

| | | | | |
|---|---|---|---|---|
| 5,308,320 A | * | 5/1994 | Safar et al. | 604/113 |
| 5,368,555 A | | 11/1994 | Sussman et al. | |
| 5,695,457 A | * | 12/1997 | St. Goar et al. | 604/27 |
| 5,800,375 A | * | 9/1998 | Sweezer et al. | 604/101.05 |
| 5,928,181 A | * | 7/1999 | Coleman et al. | 604/8 |
| 6,210,363 B1 | * | 4/2001 | Esch et al. | 604/96.01 |

OTHER PUBLICATIONS

David P. Bichell, MD, et al., Axilloaxillary Cardiopulmonary Bypass: A Practical Alternative to Femorofemoral Bypass. © 1997 by The Society of Thoracic Surgeons Published by Elsevier Science Inc., Page(s) 702–705.
Joseph F. Sabik, MD, et al., Axillary Artery: An Alternative Site of Arterial Cannulation for Patients with Extensive Aortic and Peripheral Vascular Disease, © 1995 by Mosby–Year Book, Inc., The Journal of Thoracic and Cardiovascular Surgery, pp. 886–891.
Nicholas T. Kouchoukos, et al., Perfusion for Thoracic Aortic Surgery, Section V. Clinical Application and Management of CPB, pp. 636–654.

* cited by examiner

Primary Examiner—Angela D. Sykes
Assistant Examiner—Leslie Deak
(74) Attorney, Agent, or Firm—Fulwider Patton Lee & Utecht, LLP

(57) ABSTRACT

A system for establishing differential perfusion without the use of an occlusion balloon or other flow separator devices. The flows through two lumens are controlled such that the blood flow issuing from one lumen terminating in the aortic arch supplies the entire demand of the cerebral subcirculation while the blood flow issuing from a second lumen terminating in the descending aorta supplies the entire demand of the corporeal subcirculation. When the two flows are properly balanced, an inversion layer forms therebetween and no intermixing of the two flows takes place.

32 Claims, 7 Drawing Sheets

METHODS AND DEVICES FOR PERFORMING DIFFERENTIAL PERFUSION

FIELD OF THE INVENTION

The present invention relates generally to medical devices and methods for providing differential perfusion. More particularly, the present invention pertains to novel cardiopulmonary bypass systems and to aortic catheter devices for establishing differential perfusion in a patient where selective hypothermia or hypothermia is desirable.

BACKGROUND OF THE INVENTION

Partial or full cardiopulmonary bypass (hereafter "CPB") support is needed for medical procedures requiring general anesthesia where lung function is to be arrested during routine and high-risk cardiovascular, cardioneural, neurovascular and other surgical interventions including beating, fully arrested or partially arrested cardiac procedures, to maintain cardiovascular, cardioneural and corporeal support of the respective heart, cerebral and corporeal organ systems. Such surgical interventions include treatment of aneurysms, congenital valve disease, and coronary artery disease.

In procedures where the heart is to be fully or partially arrested, it has been conventionally preferred that the heart and coronary vasculature be isolated from the rest of the cardiovascular system by application of an external cross clamp or side biting clamp. Isolation allows antegrade or retrograde perfusion of cold, warm ornormothermic oxygenated blood cardioplegia or crystalloid cardioplegia to the coronary arteries to aid in the preservation of the myocardium and to prevent dispersion of cardioplegia to the rest of the body. The heart chambers may then be vented for decompression and to create a bloodless surgical field for intracardiac interventions. For rapid cooling and arrest of the myocardium in open-chest procedures, direct application of a topical ice slush or cold pericardial lavage into the thoracic space is performed simultaneously while the cold coronary perfusion process is being accomplished.

One preferred way to accomplish CPB is to insert a venous cannula into the venous system, to withdraw deoxygenated blood into an extra corporeal circuit. A pump circulates the withdrawn blood through a blood oxygenator, heat exchanger and filter apparatus. The blood is then delivered to an aortic perfusion catheter that is inserted in the aorta of a patient.

Although CPB has been a valuable technology enabling surgical interventions, stroke and neurological deficit have been a well documented sequel as associated with the above described procedure. Recent literature has documented that the incidence of stroke is as high as 6.1% with an additional 30–79% of patients suffering from some form of cognitive deficit. Neurological deficit varies from patient to patient, however common injuries include: loss of memory, concentration and hand-eye coordination, and an increase in morbidity and mortality. The impact on the patient is significant, but factors such as age, the level of intellectual activity and the amount of physical activity pursued by the patient prior to surgery all affect the quality of life. Finally, patients who suffer from neurologic injury have a substantially prolonged hospital stay, with an attendant increase in cost (Neurological Effects of Cardiopulmonary Bypass; Rogers AT, Cardiopulmonary Bypass Principles and Practice; Gravlee GP, 21:542).

One of the likely causes of stroke and neurological deficit is the release of emboli into the blood stream during heart surgery. Potential embolic materials include atherosclerotic plaques or calcific plaques from within the aorta or cardiac valves and thrombus or clots from within the chambers of the heart. These potential emboli may be dislodged during surgical manipulation of the heart and the ascending aorta or due to high velocity jetting (sometimes called the "sandblasting effect") from the aortic perfusion cannula. In addition, application and release of an external cross clamp or side biting clamp has been shown to release emboli into the blood circulation. Other potential sources of emboli include any contact of the vessel walls with medical devices that have been introduced into the aorta. Additional sources of emboli include gaseous micro emboli formed when using a bubble oxygenator for CPB and "surgical air" that enters the heart chambers or the blood stream during surgery through open incisions or through the aortic perfusion cannula.

In an effort to reduce the deleterious effects of CPB and median sternotomies there has been much development in the area of minimally invasive cardiac surgery (MICS) to avoid the complications of CPB and the use of balloon catheters to address the clinical problems associated with a conventional median sternotomy and the attendant use of a cross clamp to occlude the ascending aorta. For example, U.S. Pat. No. Re. 35,352 to Peters describes a single balloon catheter for occluding a patient's ascending aorta and a method for inducing cardioplegic arrest. A perfusion lumen or a contralateral arterial cannula is provided for supplying oxygenated blood during cardiopulmonary bypass. U.S. Pat. No. 5,584,803 to Stevens et al. describes a single balloon catheter for inducing cardioplegic arrest and a system for providing cardiopulmonary support during closed chest cardiac surgery. A coaxial arterial cannula is provided for supplying oxygenated blood during cardiopulmonary bypass. The occlusion balloon of these catheters must be very carefully placed in the ascending aorta between the coronary arteries and the brachiocephalic artery, therefore the position of the catheter must be continuously monitored to avoid complications. Nonetheless, the deployment of balloons within the aorta may cause substantial forces to come to bear on the surrounding vessel and any shifting of such balloon may further increase the risk of dislodging embolic materials.

In clinical use, these single balloon catheters have shown a tendency to migrate in the direction of the pressure gradient within the aorta. More specifically, during infusion of cardioplegia, the balloon catheter will tend to migrate downstream due to the higher pressure on the upstream side of the balloon and, when the CPB pump is on, the balloon catheter will tend to migrate upstream into the aortic root due to the higher pressure on the downstream side of the balloon. This migration can be problematic if the balloon migrates far enough to occlude the brachiocephalic artery on the downstream side or the coronary arteries on the upstream side.

Another important development in the area of aortic balloon catheters is the concept of selective aortic perfusion. Described in commonly owned U.S. Pat. Nos. 5,308,320, 5,383,854 and 5,820,593 to Safar et al. is a method and apparatus for selective perfusion of different organ systems within the body. Other U.S. patents which address the concept of selective aortic perfusion include; U.S. Pat. No. 5,738,649, by Macoviak, U.S. Pat. Nos. 5,827,237 and 5,833,671 by Macoviak et al.; and commonly owned, copending U.S. patent application Ser. No. 08/665,635, filed Jun. 18, 1996, by Macoviak et al. All the above listed patents and patent applications, as well as all other patents referred to herein, are hereby incorporated by reference in their entirety.

Disadvantages associated with heretofore known devices and methods for establishing differential perfusion include the difficulty inherent in deploying numerous, complex devices in the vasculature, maintaining such devices in position during the procedure, avoiding the dislodgment of embolic materials and possibly the need to take steps necessary to recapture any such materials downstream. An improved device and method is needed that simplifies the deployment procedure and the efforts needed to maintain the device or devices in position while greatly reducing if not substantially obviating the risk of dislodging embolic materials. Although the foregoing discussion is primarily focused on stopped heart procedures, the present invention also has applicability in beating heart procedures including cardiac surgery and stroke.

SUMMARY OF THE INVENTION

In keeping with the foregoing discussion, the present invention provides devices and methods for establishing differential perfusion and overcomes some of the disadvantages associated with other known devices and methods. More particularly, the present invention allows for differential perfusion of circulatory subsystems by establishing differentiated blood flows without the need to deploy occlusion balloons or other flow separators. By eliminating the presence of such devices in the blood vessel, direct contact with the walls of the vessel is avoided and thus, the risk of dislodging embolic material is reduced.

Differential perfusion is achieved in accordance with the present invention by carefully adjusting the flow rates of blood delivered through multiple lumens, which have exit ports positioned in a spaced apart relationship within a blood vessel. By adjusting the relative flow rates of the two lumens a zone of zero average flow velocity is created. This zero average flow velocity or inversion layer demarks the effective separation of the two flows which may be differentiated in terms of any of a number of parameters including but not limited to temperature, degree of oxygenation or pharmacological content which is specifically altered for the purpose of providing optimal flow requirements to the targeted subsystem.

In the preferred embodiments, two lumens are positioned in the aorta such that one exit port(s) is positioned in the aortic arch and the other exit port(s) is positioned in the descending aorta. By adjusting the relative flow rates through the two lumens, either through manipulating the flows of an external pump, clamping output channels or by lumen size and output configurations, an inversion layer is established downstream of the left subclavian artery. The cerebral and corporeal subcirculation effectively become segmented to facilitate the differentiated support of such subsystems. Optionally, a third lumen can be positioned in the vena cava or right atrium to serve as a means for withdrawing deoxygenated blood from the patient for reoxygenation and differential reconditioning which will be returned to the aorta through the two lumens of the aortic catheter(s). The present invention contemplates the use of a single blood pump and at least one heat exchanger, at least one oxygenator and various inline arterial filters. By employing a single pump, the complexity of the system is greatly reduced and equalization of output pressures is more easily attainable. Unique pumping systems can be used to attain desirable results. For example an integral heat exchanger and oxygenator located before or after separation into arch and corporeal flows can be used with an addition heat exchanger for the arch circulation. The temperature of withdrawn deoxygenated tepid blood is easily adjusted through a heat exchanger and oxygenator to achieve the desired differentiation.

Various catheter configurations may be employed to achieve the desired placement in the aorta. For example, a single catheter comprising two lumens or two catheters having a single lumen may be employed to deliver the two differentiated flows to the aorta wherein the single device configuration allows for a constant distance separation of the exit ports, while the latter configuration has the additional benefit of allowing the relative spacing of the two sets of exit ports to be altered in an effort to more readily accommodate variations in patient anatomies. The catheters may be introduced peripherally, for example the femoral, brachial, iliac, subdlavian, radial or carotid artery, through an intercostal space or centrally via an aortotomy, or via a combination of both.

After proper placement is verified through the use of TEE, transillumination, infrared or other means, the surgeon generally begins CPB and starts perfusing the aorta prior to application of an external cross-clamp or internal cross-clamp to the ascending aorta. Once minimum proper perfusion flow has been established the surgeon will apply the cross-clamp to the aorta or use a valve or inflate an occlusion balloon inside the aorta and supply crystalloid cardioplegia or blood cardioplegia to the myocardium to completely or partially arrest the heart. By advantageously adjusting the relative flow rates through the two perfusion lumens or by adjusting their relative positions in situ or by predetermining out flow port position, an inversion layer is created just downstream of the left subclavian artery. The inversion layer can be moved either upstream or downstream by adjusting relative flow rates or by adjusting the relative positions of the lumens and outflow ports to achieve the desired position. For example, the inversion layer may form in the aortic arch creating superior flow to the arch vessels and inferior flow to the corporeal circulation. In one preferred embodiment, flow delivered upstream of the inversion layer, hypothermic oxygenated blood is perfused to the arch vessels through the arch perfusion ports. Downstream of the inversion layer, normothermic oxygenated blood is perfused to the corporeal circulation through the corporeal perfusion ports. Upstream of the cross-clamp or occlusion balloon, cardioplegia is supplied to keep the heart in a partially or completely arrested state.

By establishing differential perfusion in accordance with the present invention, the clinician is able to isolate the cerebral circulation from the corporeal circulation and thereby facilitate the creation of a neuroprotective environment through temperature, pressure and chemical control, allowing the brain to be cooled to a significantly lower temperature than the body. Lowering the temperature of the brain allows the blood flow to the brain to be reduced since the metabolic demands of the tissue for oxygen are reduced. The reduction in flow, volume and cycles of blood to the brain provides less opportunity for emboli to be introduced into the cerebral blood circulation during surgical interventions. In addition, prolonged hypothermia for the brain while the body is warm extends the neuroprotective period while avoiding issues associated with systemic hypothermia, such as coagulopathy, low cardiac output and prolonged Intensive Care Unit time.

These and other features and advantages of the present invention will become apparent from the following detailed description of preferred embodiments which, taken in conjunction with the accompanying drawings, illustrate by way of example the principles of the invention.

DETAILED DESCRIPTION OF THE INVENTION

Figure 1:
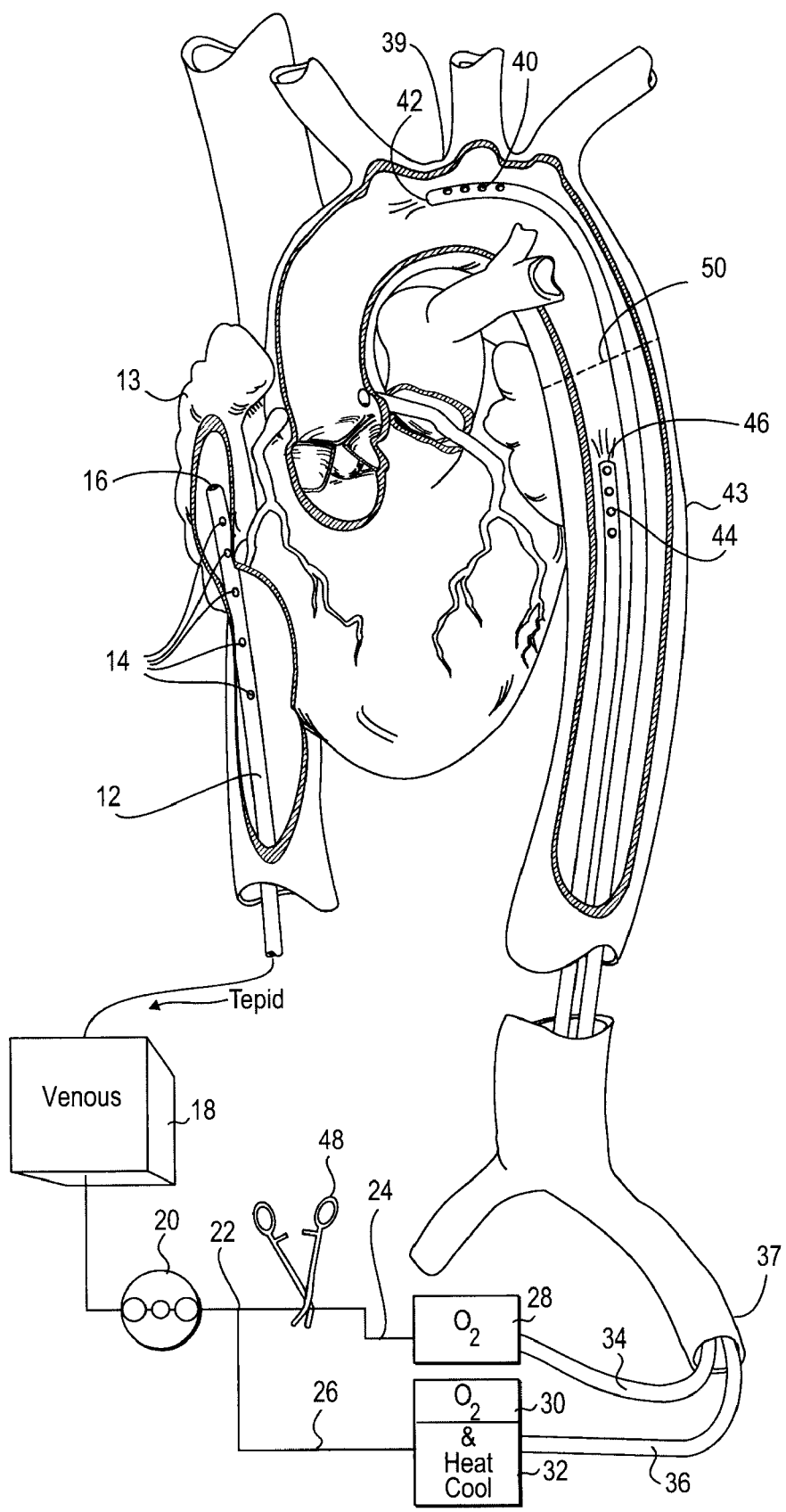
FIG. 1 is a semi-schematic illustration of a preferred embodiment configuration of the present invention wherein two single lumen perfusion catheters are introduced femorally.

The FIGS generally illustrate the devices and methods of the present invention that are employed to establish differential perfusion. In all embodiments, deoxygenated blood is withdrawn from the venous system and is thereafter split into two flows, which are differentially conditioned and returned to the patient's arterial system. The two differentially conditioned flows are introduced into the aorta in a spaced apart relationship and the relative flow rates are adjusted such that one flow supplies substantially the entire cerebral demand and the other flow supplies substantially the entire corporeal demand with minimal intermixing. In alternative embodiments, oxygenated blood could be withdrawn from the patient through a third lumen and conditioned and introduced into the patients arterial system in beating heart applications.

Common to all of the illustrated embodiments is the placement and configuration of a venous catheter 12 and its corresponding lumen through which deoxygenated blood is extracted from the patient. The venous catheter 12 is positioned in the vena cava 13 and or right atrium by any number of well known techniques including the Seldinger technique, the use of peripheral veins as well as directly into the right atrium through a median sternotomy, mini-thoracotomy or through an intercostal space. A plurality of ports 14 formed near the distal end of the catheter that allow for the unobstructed flow of blood into the internal lumen of the venous catheter 12. An opening 16 at the distal end of the catheter facilitates its optional advancement along a guidewire. The tepid blood is withdrawn into a venous reservoir 18 from which it is subsequently conditioned and returned to the body.

FIG. 1 is a semi-schematic illustration of a first embodiment of the present invention wherein two single lumen perfusion catheters are employed to deliver differentially conditioned blood to the aorta. In alternative embodiments a second lumen can be provided to facilitate placement of a guidewire or other medical device to measure temperature, pressure or chemical composition. A venous catheter 12 directs tepid deoxygenated blood to a venous reservoir. Blood is then pumped by pumping means 20 to a Y-junction 22 where it is separated into two separate flows 24, 26 each of which is subsequently oxygenated by separate oxygenators 28 and 30. Additionally, this particular embodiment employs a single heat exchanger 32 with which the temperature of the flow destined for cerebral support is adjusted. Any of a number of different conditioning devices can be employed to condition one or both of the blood flows. In this particular embodiment both perfusion catheters 34, 36 are introduced through the same femoral artery 37. The cerebral support catheter 36 through which the temperature adjusted blood flow is to flow is advanced in a retrograde direction until it is positioned in the aortic arch 39. Perfusion ports 40 are formed near the distal end of the catheter to allow the perfusion of blood therefrom. An opening 42 formed in the distal end of the catheter facilitates its advancement into position along a guidewire. The corporeal support catheter 34 is advanced in a retrograde direction until positioned within the descending aorta 43, abdominal thoracic aorta or anywhere downstream of the left subclavian artery. Perfusion ports 44 are formed near its distal end to allow perfusion of blood therefrom. An opening 46 formed in the distal end of the catheter facilitates its advancement into position along a guidewire.

The cerebral support catheter 36 may be formed from a flexible thermoplastic material, a thermoplastic elastomer or a thermoset elastomer. More specifically, suitable materials for the cerebral support catheter 36 include, but are not limited to, PEBAX, PVC, PET, polystyrene, polyvinylchloride, polyurethane, polyethylene, polypropylene, polyamides (nylons), copolymers, polyesters, silicone, latex, and combinations thereof, as well as braided, coiled or counterwound wire reinforcement or filament reinforced composites. Alternatively, or in combination therewith, the cerebral support catheter 36 may be made of thin walled metallic tubing or hypotube, such as stainless steel, platinum, titanium, nitinol, alloys or Cobalt alloys such as Elgiloy and Carpenter MP 35.

The cerebral support catheter 36 has an outer diameter of about 5 to about 16 French and an inner diameter of approximately 0,053" to about 0.200" and has approximately one to twelve exit ports 40 formed therein, each approximately 0.039" to about 0.095" in diameter. The number of port(s) needed is correlative to the size of the ports as well as the lumen diameter and flow requirements. The combination of tubing diameter and port diameters must be able to yield a flow of approximately 0.5 L/min to about 2.0 L/min with about 25 mm Hg to about 200 mm Hg of pressure for the arch circulation. The catheter is preferably curved near its distal end to match the curvature of the aorta and is preferably reinforced with a helical winding of stainless steel wire or braided reinforcement. Such reinforcement should be spaced sufficiently apart in the location near the distal end of the catheter in order to accommodate the exit ports 40 residing therebetween. The corporeal support catheter 34 may similarly be formed of the same materials having an inner diameter and a sufficient number of holes to yield a flow of approximately three times that of the cerebral support catheter, i.e. approximately 1.5 L/min to about 6.0 L/min with about 25 mm Hg to about 200 mm Hg of pressure. The catheter may be similarly reinforced with a helical or braided coil of stainless steel wire.

Upon institution of perfusion, blood issues from the ports 40, 44 of both perfusion catheters 36, 34 respectively. The catheters may have a predesigned configuration such that no matter what the ultimate flow of the extra corporeal bypass system the consistent ratios of flow are maintained. Alternatively, by adjusting the relative flows through the two catheters externally, such as with the use of a clamp 48 to constrict one or both of the conduits 24, 26, the physician can substantially match the flow requirements of the cerebral and corporeal subcirculation respectively, creating a state of equilibrium wherein the two flows remain separated by an inversion layer 50 that forms within the aorta. A cerebral to corporeal flow ratio of approximately 1:3 is required in order to reach a state of equilibrium whereby an inversion layer 50 is formed downstream of the left subclavian. An excessive flow rate issuing from the cerebral support catheter 36 will cause the superfluous volume to flow downwardly into the corporeal subcirculation tending to move the inversion layer downstream. Conversely, an excessive flow rate issuing from the corporeal support catheter 34 will cause the excessive volume to flow upwardly into the cerebral subcirculation tending to move the inversion layer upstream. In certain applications, slightly excessive cerebral flow rate may be desirable in order to ensure that an adequate supply of the blood conditioned for the cerebral subcirculation is actually delivered to the cerebral subcirculation, while any excess delivered into the corporeal subcirculation is quickly diluted by the substantially greater flow and volume associated with the corporeal vasculature. Alternatively, another lumen may be added to either catheter to provide blood flow to another organ system differentially from the other two.

Figure 2:
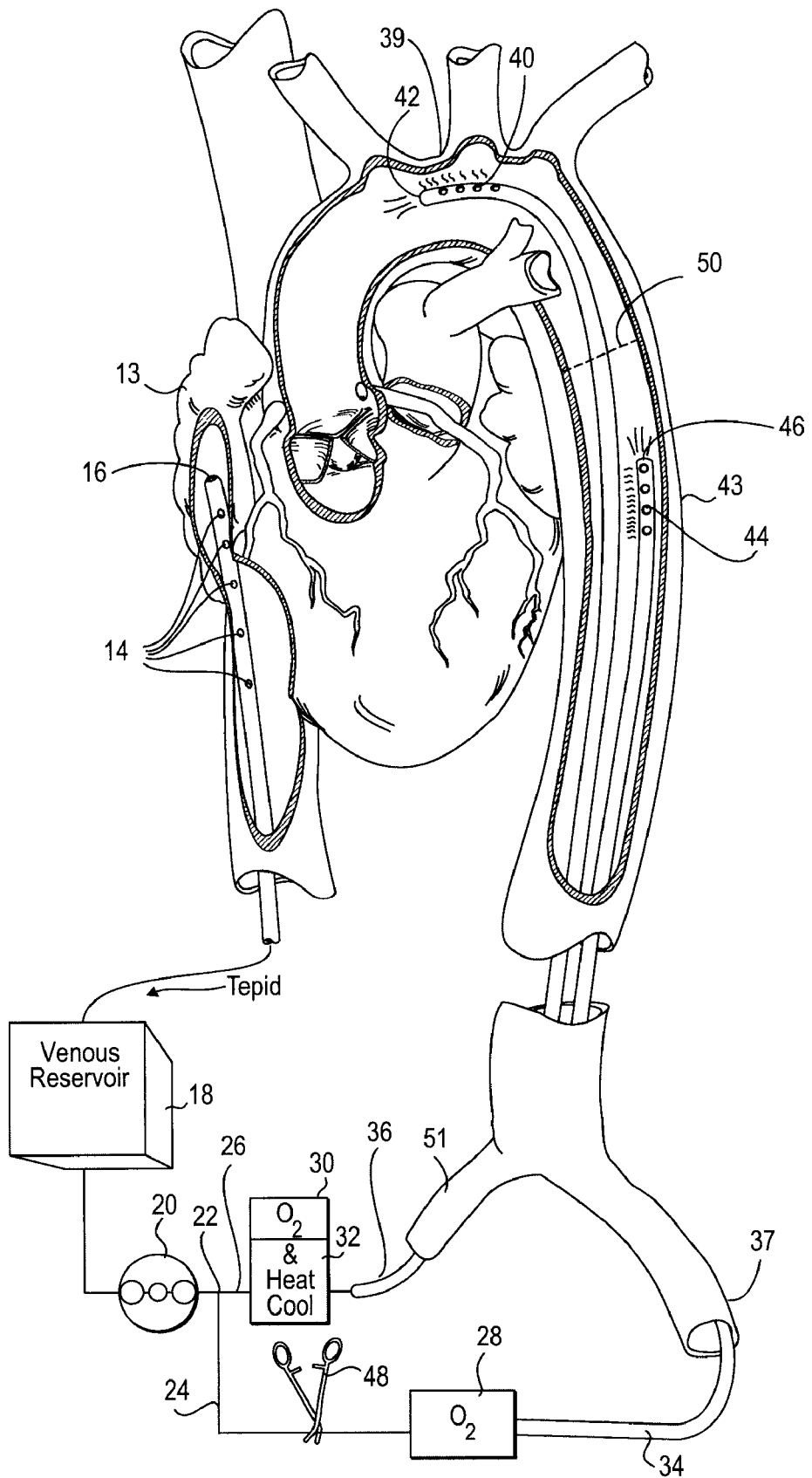
FIG. 2 is a semi-schematic illustration of an alternative embodiment configuration of the present invention wherein two single lumen perfusion catheters are introduced femorally.

FIG. 2 is a semi-schematic illustration of a second embodiment of the present invention wherein two single lumen perfusion catheters are employed to deliver differentially conditioned blood to the aorta. Blood is withdrawn from the venous reservoir by a blood pump 20 after which a Y-fitting 22 splits the pump output into two separate flows 24, 26 each of which is subsequently oxygenated by a separate oxygenator 28 and 30. Additionally, this particular embodiment employs a single heat exchanger 32 with which the temperature of the flow destined for cerebral support is adjusted. Any of a number of different conditioning devices can be called upon to condition one or both blood flows. In this particular embodiment one perfusion catheter 34 is introduced through one femoral artery 37 while the other perfusion catheter is introduced through the other femoral artery 51. The cerebral support catheter 36 through which the temperature adjusted blood flow is to flow is advanced in a retrograde direction so as to terminate in the aortic arch 39. Perfusion ports 40 are formed near the distal end of the catheter to allow the escape of blood therefrom. An opening 42 formed in the distal end of the catheter facilitates its advancement into position along a guidewire. The corporeal support catheter 34 is advanced in a retrograde direction into position within the descending aorta 43. Perfusion ports 44 are formed near its distal end to allow the escape of blood therefrom. An opening 46 formed in the distal end of the catheter facilitates its advancement into position along a guidewire.

The cerebral support catheter 36 may be formed from a flexible thermoplastic material, a thermoplastic elastomer or a thermoset elastomer. More specifically, suitable materials for the cerebral support catheter 36 include, but are not limited to, PEBAX, PVC, PET, polystyrene, polyvinylchloride, polyurethane, polyethylene, polypropylene, polyamides (nylons), copolymers, polyesters, silicone, latex, and combinations thereof, as well as braided, coiled or counterwound wire reinforcement or filament reinforced composites. Alternatively, or in combination therewith, the cerebral support catheter 36 may be made of thin walled metallic tubing or hypotube, such as stainless steel, platinum, titanium, nitinol, alloys or Cobalt alloys such as Elgiloy and Carpenter MP 35.

The cerebral support catheter 36 has an outer diameter of about 5 to about 16 French and an inner diameter of approximately 0,053" to about 0.200" and has approximately one to twelve exit ports 40 formed therein, each approximately 0.039" to about 0.095" in diameter. The number of port needed is correlative to the size of the ports as well as the lumen diameter and flow requirements. The combination of tubing diameter and port diameters must be able to yield a flow of approximately 0.5 L/min to about 2.0 L/min with about 5 mm Hg to about 200 mm Hg of pressure for the arch circulation. The catheter is preferably curved near its distal end to match the curvature of the aorta and is preferably reinforced with a helical winding of stainless steel wire or braided reinforcement. Such reinforcement should be spaced sufficiently apart in the location near the distal end of the catheter in order to accommodate the exit ports 40 residing therebetween. The corporeal support catheter 34 may similarly be formed of the same materials having an inner diameter and a sufficient number of holes to yield a flow of approximately three times that of the cerebral support catheter, i.e. approximately 1.5 L/min to about 6.0 L/min with about 25 mm Hg to about 200 mm Hg of pressure. The catheter may be similarly reinforced with a helical or braided coil of stainless steel wire.

Upon energization of pump 20, blood issues from the ports 40, 44 of both perfusion catheters 36, 34. By adjusting the relative flows through the two catheters, such as with the use of a clamp 48, switch or variable resistor, to constrict one or both of the conduits 24, 26, so as to substantially match the flows to the requirements of the cerebral and corporeal subcirculation respectively, a state of equilibrium is achieved wherein the two flows remain separated by an inversion layer 50 that forms therebetween in the aorta. A cerebral to corporeal flow ratio of approximately 1:3 is required in order to reach a state of equilibrium whereby an inversion layer 50 is formed. An excessive flow rate issuing from the cerebral support catheter 36 will cause the superfluous volume to flow downwardly into the corporeal subcirculation. Conversely, an excessive flow rate issuing from the corporeal support catheter 34 will cause the superfluous volume to flow upwardly into the cerebral subcirculation. In certain applications, a slightly excessive cerebral flow rate may be desirable in order to ensure that an adequate supply of the blood conditioned for the cerebral subcirculation is actually delivered to the cerebral subcirculation, while any excess delivered into the corporeal subcirculation is quickly diluted by the substantially greater flow and volume associated with the corporeal vasculature.

Figures 3, 4, 5:
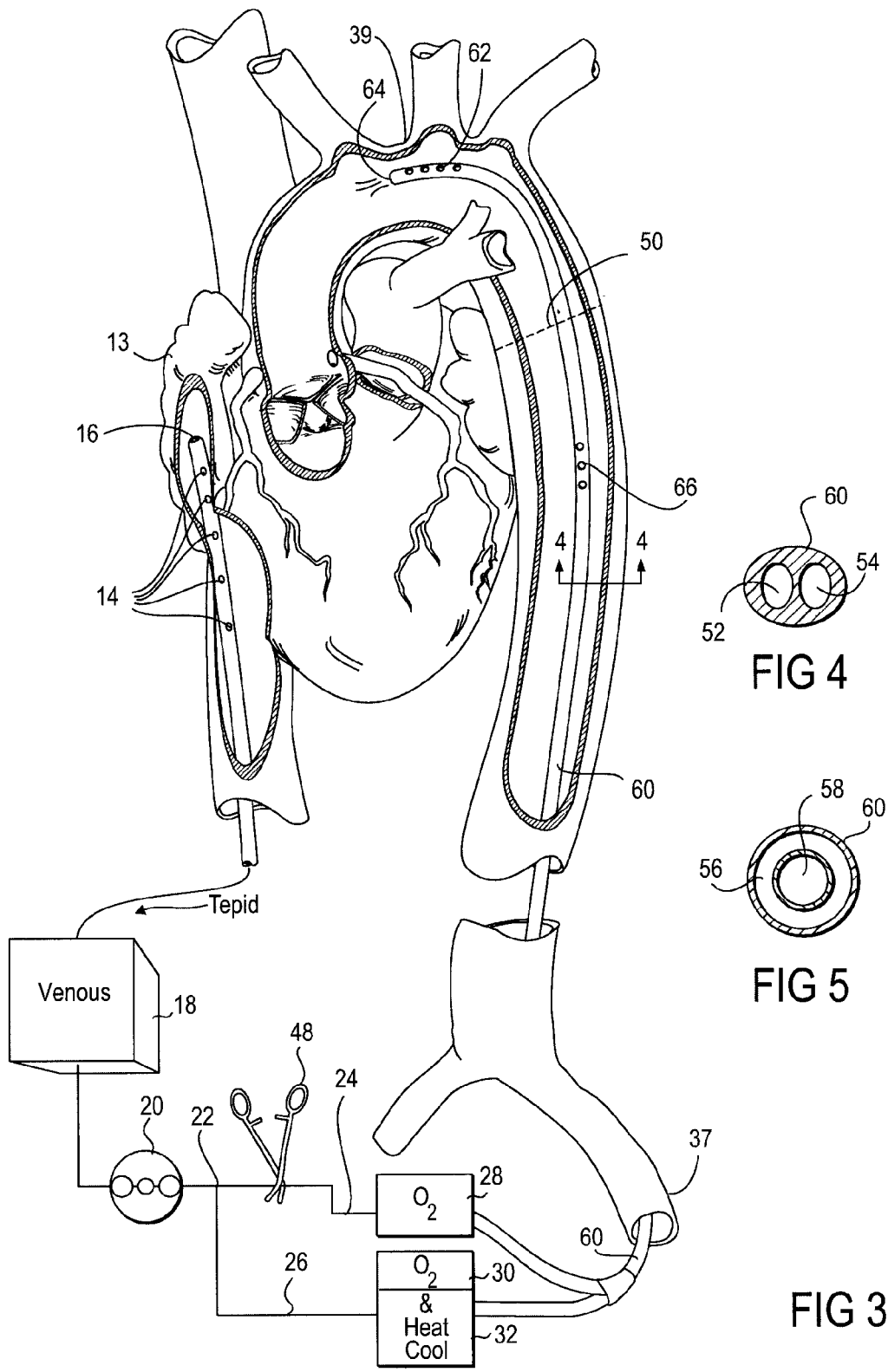
FIG. 3 is a semi-schematic illustration of another alternative embodiment configuration of the present invention wherein a single dual lumen perfusion catheter is introduced femorally.
FIG. 4 is a cross-sectional view of a dual lumen perfusion catheter taken along lines 4—4 of FIG. 3.
FIG. 5 is a cross-sectional view of an alternative embodiment dual lumen perfusion catheter.

FIG. 3 is a semi-schematic illustration of an embodiment of the present invention wherein a single, dual lumen perfusion catheter is employed to deliver differentially conditioned blood to the aorta. Tepid blood is withdrawn from the venous reservoir by a blood pump 20 after which a Y-fitting 22 splits the pump output into two separate flows 24, 26 each of which is subsequently oxygenated by a separate oxygenator 28 and 30. Additionally, this particular embodiment employs a single heat exchanger 32 with which the temperature of the flow destined for cerebral support is adjusted. Any of a number of different conditioning devices can be employed to condition one or both flows. In this particular embodiment, both conditioned blood flows are then conducted into the two lumens 52 and 54 or 56 and 58 of the aortic perfusion catheter 60 which is introduced into the vasculature through the femoral artery 37. The two lumens within the aortic catheter may be arranged in a parallel arrangement 52, 54 as is shown in FIG. 4 or alternatively, in a coaxial arrangement 56, 58 as is illustrated in FIG. 5. The catheter 60 is advanced in a retrograde direction so as to terminate in the aortic arch 39. Cerebral support perfusion ports 62 are formed near the distal end of the catheter to allow the escape of blood from the lumen carrying the blood condition for cerebral support. In a coaxial lumen arrangement as is illustrated in FIG. 5, the central lumen 58 would be in fluid communication with such ports. An opening 64 formed in the distal end of the catheter facilitates its advancement into position along a guidewire. Corporeal support perfusion ports 66 are formed proximally relative to the cerebral support perfusion ports. In a coaxial arrangement as is illustrated in FIG. 5, the outer lumen would be in fluid communication with such ports.

The catheter 60 may be formed of the same materials described in connection with FIGS. 1 and 2 and preferably is constructed with helical winding stainless steel wire reinforcement. The two lumens 52, 54 or 56, 58 and the perfusion ports 62, 66 are sized and dimensioned to permit approximately three times as much flow to be delivered to the corporeal subcirculation as to the cerebral subcirculation. The cerebral support lumen and associated perfusion ports 62 should be capable of delivering approximately 0.5 L/min to about 2.0 L/min at 5 mm Hg to about 200 mm Hg of pressure while the corporeal support lumen and associated perfusion ports 66 should be capable of delivering approximately 1.5 L/min to about 6.0 L/min at 5 mm Hg to about 200 mm Hg of pressure. Various combinations of lumen diameter and perfusion port size and quantity can be selected to achieve such flows. The catheter is preferably curved near its distal end to match the curvature of the aorta.

Upon energization of pump 20, blood issues from the ports 62, 66. By adjusting the relative flows through the two conduits, such as with the use of a clamp 48 to constrict one or both of the conduits 24, 26, so as to substantially match the flows to the requirements of the cerebral and corporeal subcirculation respectively, a state of equilibrium is achieved wherein the two flows remain separated by an inversion layer 50 that forms therebetween in the aorta. A cerebral to corporeal flow ratio of approximately 1:3 is required in order to reach a state of equilibrium whereby an inversion layer 50 is formed. An excessive flow rate issuing from the cerebral support perfusion ports 62 will cause the superfluous volume to flow downwardly into the corporeal subcirculation. Conversely, an excessive flow rate issuing from the corporeal support perfusion ports 66 will cause the superfluous volume to flow upwardly into the cerebral subcirculation. In certain applications, a slightly excessive cerebral support flow rate may be desirable in order to ensure that an adequate supply of the blood conditioned for the cerebral subcirculation is actually delivered to the cerebral subcirculation, while any excess delivered into the corporeal subcirculation is quickly diluted by the substantially greater flow and volume associated with the corporeal vasculature.

Figure 6:
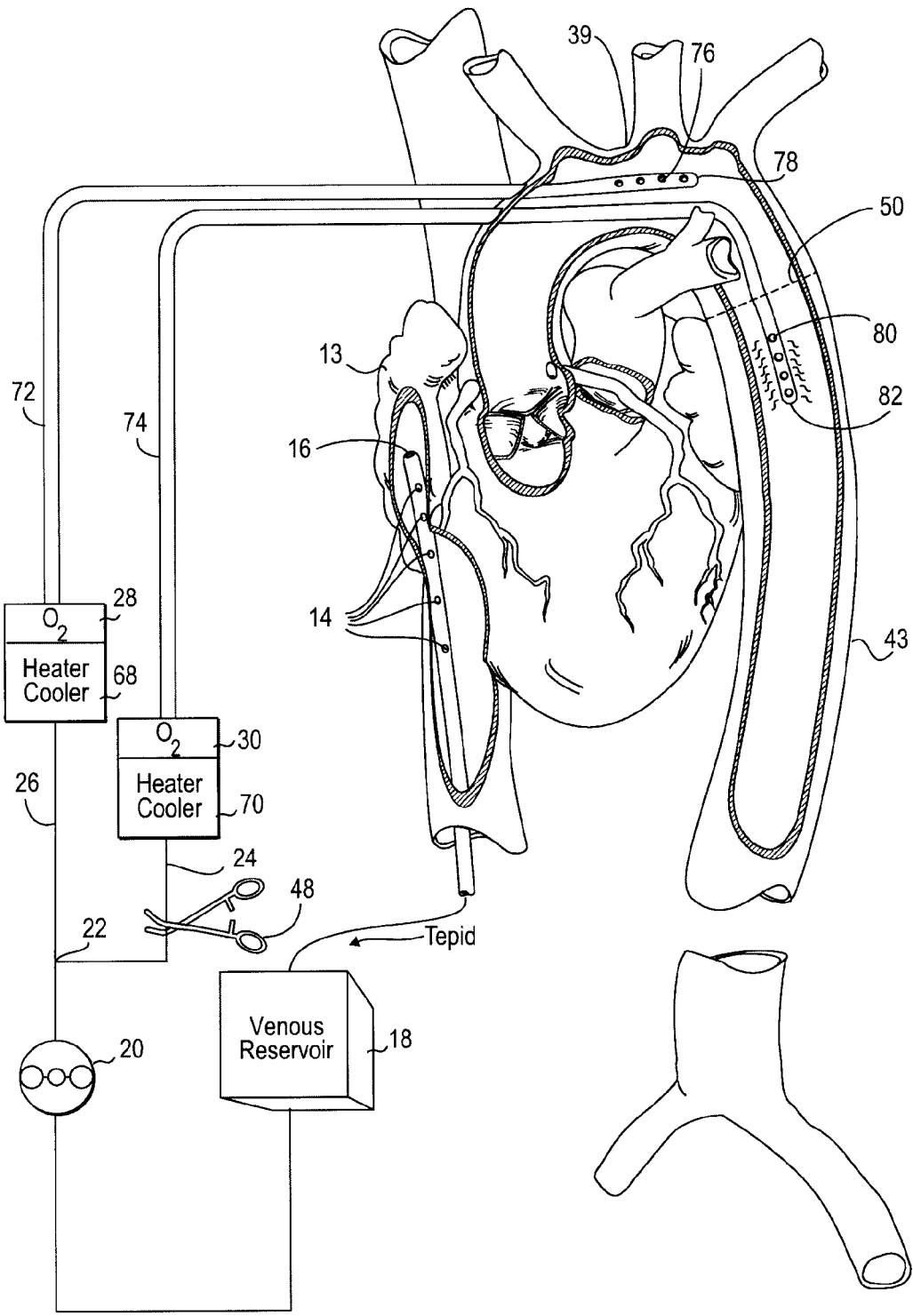
FIG. 6 is a semi-schematic illustration of another alternative embodiment configuration of the present invention wherein two single lumen perfusion catheters are introduced via an aortotomy.

FIG. 6 is a semi-schematic illustration of another embodiment of the present invention wherein two single lumen perfusion catheters are employed to deliver differentially conditioned blood to the aorta. Blood is withdrawn from the venous reservoir by a blood pump 20 after which a Y-fitting 22 splits the pump output into two separate flows 24, 26 each of which is subsequently oxygenated by a separate oxygenator 28 and 30. Additionally, this particular embodiment employs two heat exchangers 68 and 70 with which the temperature of each flow can be independently adjusted. Alternatively, a single heat exchanger may be employed, preferably for the flow destined for cerebral support. Additionally, any number of blood conditioning devices can be included in one or both blood flows. In this particular embodiment both perfusion catheters 72, 74 are introduced directly into the aorta via an aortotomy either through a single penetration site where the two catheters are collateral or coaxial with telescoping properties or two penetration sites as illustrated. The cerebral support catheter 72 is advanced in an antegrade direction so as to terminate in the aortic arch 39. Perfusion ports 76 are formed near the distal end of the catheter to allow the escape of blood therefrom. An opening 78 formed in the distal end of the catheter facilitates its advancement into position along a guidewire. The perfusion catheter 74 intended for corporeal support is advanced in an antegrade direction into position within the descending aorta 43. Perfusion ports 80 are formed near its distal end to allow the escape of blood therefrom. An opening 82 formed in the distal end of the catheter facilitates its advancement into position along a guidewire.

The cerebral support catheter 72 may be formed of the same materials described in connection with FIGS. 1 and 2 has an outer diameter of about 5 to about 16 French and an inner diameter of approximately 0.053" to about 0.200" and has approximately one to twelve exit ports 76 formed therein, each approximately 0.039" to about 0.095" in diameter. The number of port(s) needed is correlative to the size of the port(s) as well as the lumen diameter and flow requirements. The combination of tubing diameter and port diameters must be able to yield a flow of approximately 0.5 L/min to about 2.0 L/min with about 5 mm Hg to about 200 mm Hg of pressure for the arch circulation. The catheter is preferably curved to match the curvature of the aorta and is preferably reinforced with a helical winding of stainless steel wire or braided reinforcement. Such reinforcement should be spaced sufficiently apart in the location near the distal end of the catheter in order to accommodate the exit ports 40 residing therebetween. The corporeal support catheter 74 may similarly be formed of the same materials having an inner diameter and a sufficient number of holes to yield a flow of approximately three times that of the cerebral support catheter, i.e. approximately 1.5 L/min to about 6.0 L/min with about 25 mm Hg to about 200 mm Hg of pressure. The catheter may be similarly reinforced with a helical or braided coil of stainless steel wire.

Upon energization of pump 20, blood issues from the ports 76, 80 of both perfusion catheters 72, 74. By adjusting the relative flows through the two catheters, such as with the use of a clamp 48 to constrict one or both of the conduits 26, 24, so as to substantially match the requirements of the cerebral and corporeal subcirculation respectively, a state of equilibrium is achieved wherein the two flows remain separated by an inversion layer 50 that forms therebetween. A cerebral to corporeal flow ratio of approximately 1:3 is required in order to reach a state of equilibrium whereby an inversion layer 50 is formed. An excessive flow rate issuing from the cerebral support catheter 72 will cause the superfluous volume to flow downwardly into the corporeal subcirculation. Conversely, an excessive flow rate issuing from the corporeal support catheter 74 will cause the superfluous volume to flow upwardly into the cerebral subcirculation. In certain applications, slightly excessive cerebral flow rate may be desirable in order to ensure that an adequate supply of the blood conditioned for the cerebral subcirculation is actually delivered to the cerebral subcirculation, while any excess delivered into the corporeal subcirculation is quickly diluted by the substantially greater flow and volume associated with the corporeal vasculature.

Figure 7:
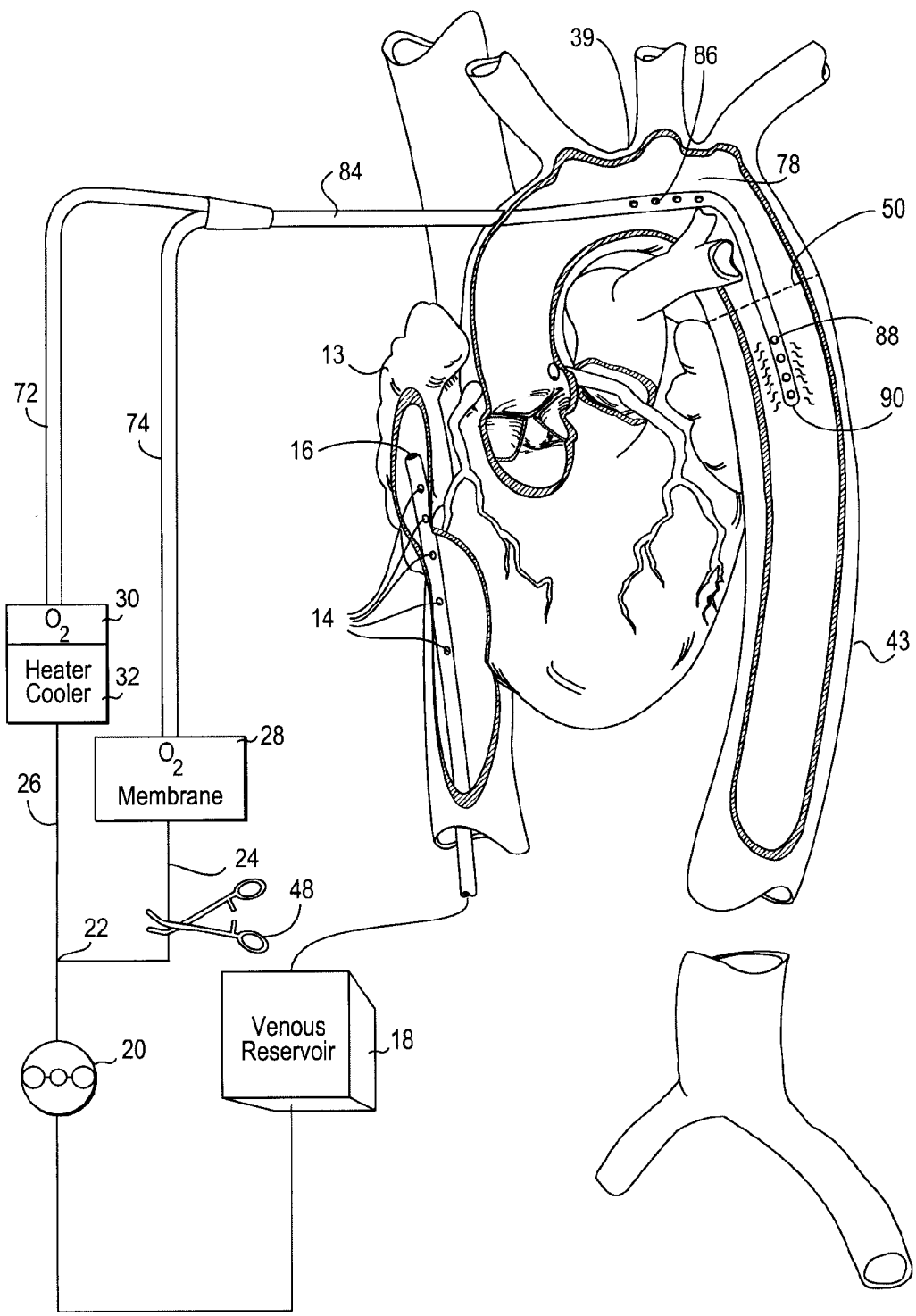
FIG. 7 is a semi-schematic illustration of another alternative embodiment configuration of the present invention wherein a single dual lumen perfusion catheter is introduced via an aortotomy.

FIG. 7 is a semi-schematic illustration of another embodiment of the present invention wherein a single dual lumen perfusion catheter is employed to deliver differentially conditioned blood to the aorta. Blood is withdrawn from the venous reservoir 18 by a blood pump 20 after which a Y-fitting 22 splits the pump output into two separate flows 24, 26 each of which is subsequently oxygenated by a separate oxygenator 28 and 30. Additionally, this particular embodiment employs a single heat exchanger 32 with which the temperature of the flow destined for cerebral support is adjusted. Any of a number of different conditioning devices can be employed to condition one or both flows. In this particular embodiment the two flows are then conducted into the two lumens of a dual lumen catheter wherein the lumens may be arranged coaxially as is shown in FIG. 5, either fixed or slidable or arranged in parallel to one another as is shown in FIG. 4. In this particular embodiment the catheter 84 is introduced into the aorta directly. The catheter is advanced in an antegrade direction such that the cerebral support perfusion ports 86 are positioned within the aortic arch 39 and the corporeal support perfusion ports 88 are positioned in the descending aorta 43. In the coaxial arrangement shown in FIG. 5, the central lumen would carry the blood flow intended for corporeal support. An opening 90 formed in the distal end of the catheter facilitates its advancement along a guidewire if so desired.

The catheter 84 may be formed of the same materials described in connection with FIGS. 1 and 2 and in a preferred embodiment implements helical winding of stainless steel wire therein. The two lumens and perfusion ports associated with each lumen are dimensioned to permit approximately three times as much flow to be delivered to the corporeal subcirculation as to the cerebral subcirculation and are proportioned in a similar manner as the previous embodiments.

Upon energization of pump 20, blood issues from the ports 86, 88 of perfusion catheter 84. By adjusting the relative flows through the two lumens, such as with the use of a clamp 48 to constrict one or both of the conduits 24, 26, so as to substantially match the requirements of the cerebral and corporeal subcirculation respectively, a state of equilibrium is achieved wherein the two flows remain separated by an inversion layer 50 that forms therebetween in the aorta. A cerebral to corporeal flow ratio of approximately 1:3 is required in order to reach a state of equilibrium whereby the inversion layer 50 is formed. An excessive flow rate issuing from the cerebral perfusion ports 86 will cause the superfluous volume to flow downwardly into the corporeal subcirculation. Conversely, an excessive flow rate issuing from the corporeal perfusion ports 88 will cause the superfluous volume to flow upwardly into the cerebral subcirculation. In certain applications, a slightly excessive cerebral flow rate may be desirable in order to ensure that an adequate supply of the blood conditioned for the cerebral subcirculation is actually delivered to the cerebral subcirculation, while any excess delivered into the corporeal subcirculation is quickly diluted by the substantially greater flow and volume associated with the corporeal vasculature.

Figure 8:
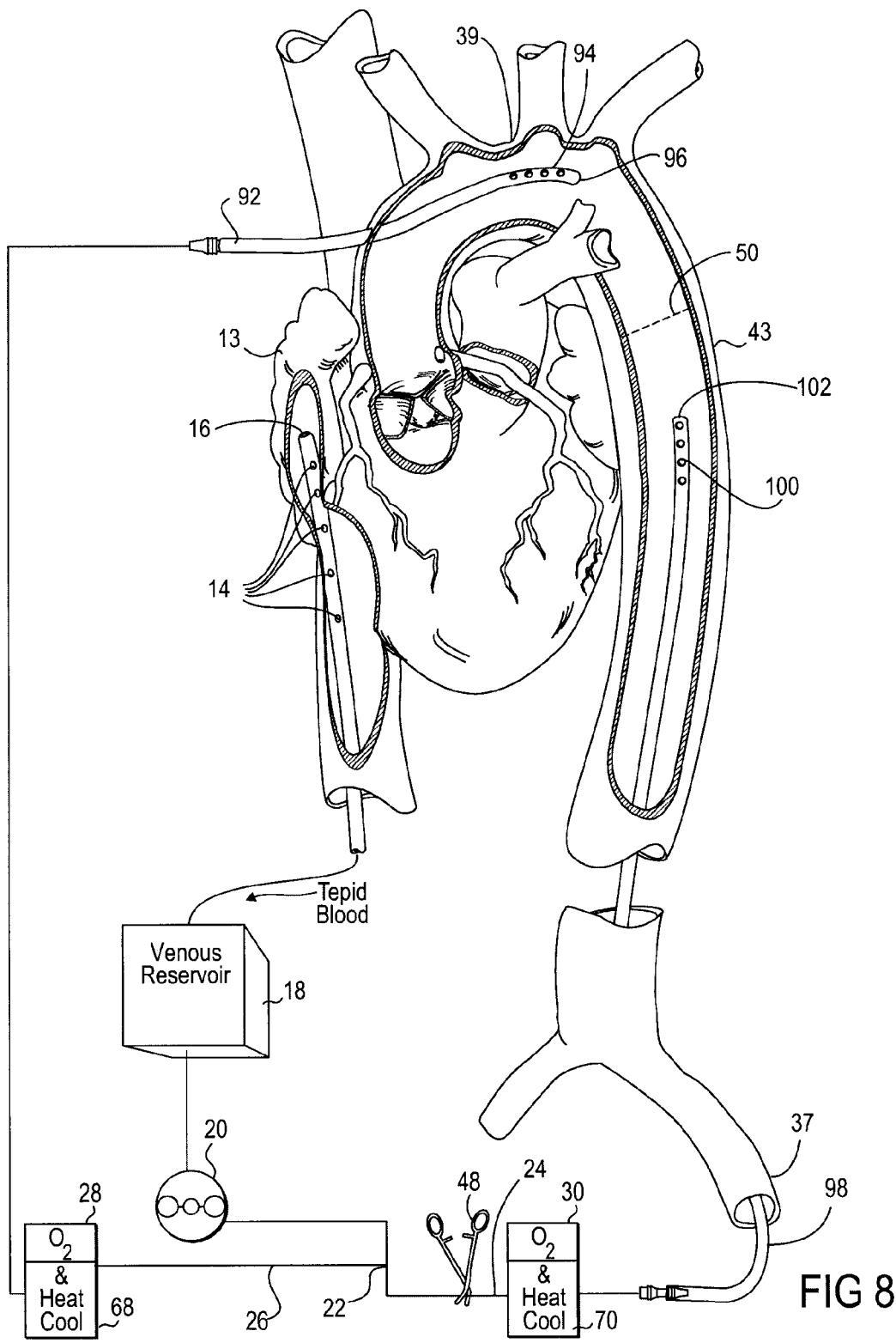
FIG. 8 is a semi-schematic illustration of another alternative embodiment configuration of the present invention wherein a first single lumen perfusion catheter is introduced femorally and a second single lumen perfusion catheter is introduced via an aortotomy.

FIG. 8 is a semi-schematic illustration of another embodiment of the present invention wherein two single lumen perfusion catheters are employed to deliver differentially conditioned blood to the aorta. Blood is withdrawn from the venous reservoir by a blood pump 20 after which a Y-fitting 22 splits the pump output into two separate flows 24, 26 each of which is subsequently oxygenated by a separate oxygenator 28 and 30. Additionally, this particular embodiment employs a heat exchanger 68, 70 for each flow. Alternatively, a single heat exchanger may be used, preferably on the branch for providing cerebral support. Additionally, any number of different conditioning devices may be employed to condition one or both flows. In this particular embodiment, the cerebral support catheter 92 is introduced directly into the aorta via aortotomy and advanced in an antegrade direction such that perfusion ports 94, formed near its distal end of the catheter, are positioned within the aortic arch. The perfusion ports allow the escape of blood therefrom. An opening 96 formed in its distal end facilitates the advancement of the catheter over a guidewire. The corporeal support catheter 98 is introduced into the vasculature through the femoral artery 37 and advanced in a retrograde direction to a position in which perfusion ports 100 are located within the descending aorta 43. The perfusion ports allow the escape of blood therefrom. An opening 102 formed in the distal end facilitates its advancement over a guidewire.

The cerebral support catheter 92 is similar in construction and dimensions to the cerebral support catheter 72 of FIG. 6 and the corporeal support catheter 98 is similar in construction and dimensions to the corporeal support catheter 34 of FIG. 2.

Upon energization of pump 20, blood issues from the ports 94, 100 of both perfusion catheters 92, 98. By adjusting the relative flows through the two catheters, such as with the use of a clamp 48 to constrict one or both of the conduits 24, 26, so as to substantially match the requirements of the cerebral and corporeal subcirculation respectively, a state of equilibrium is achieved wherein the two flows remain separated by an inversion layer 50 that forms therebetween in the aorta. A cerebral to corporeal flow ratio of approximately 1:3 is required in order to reach a state of equilibrium whereby the inversion layer 50 is formed. An excessive flow rate issuing from the cerebral support catheter will cause the superfluous volume to flow downwardly into the corporeal subcirculation. Conversely, an excessive flow rate issuing from the corporeal support catheter will cause the superfluous volume to flow upwardly into the cerebral subcirculation. In certain applications, a slightly excessive cerebral support flow rate may be desirable in order to ensure that an adequate supply of the blood conditioned for the cerebral subcirculation is actually delivered to the cerebral subcirculation, while any excess delivered into the corporeal subcirculation is quickly diluted by the substantially greater flow and volume associated with the corporeal vasculature.

Figure 9:
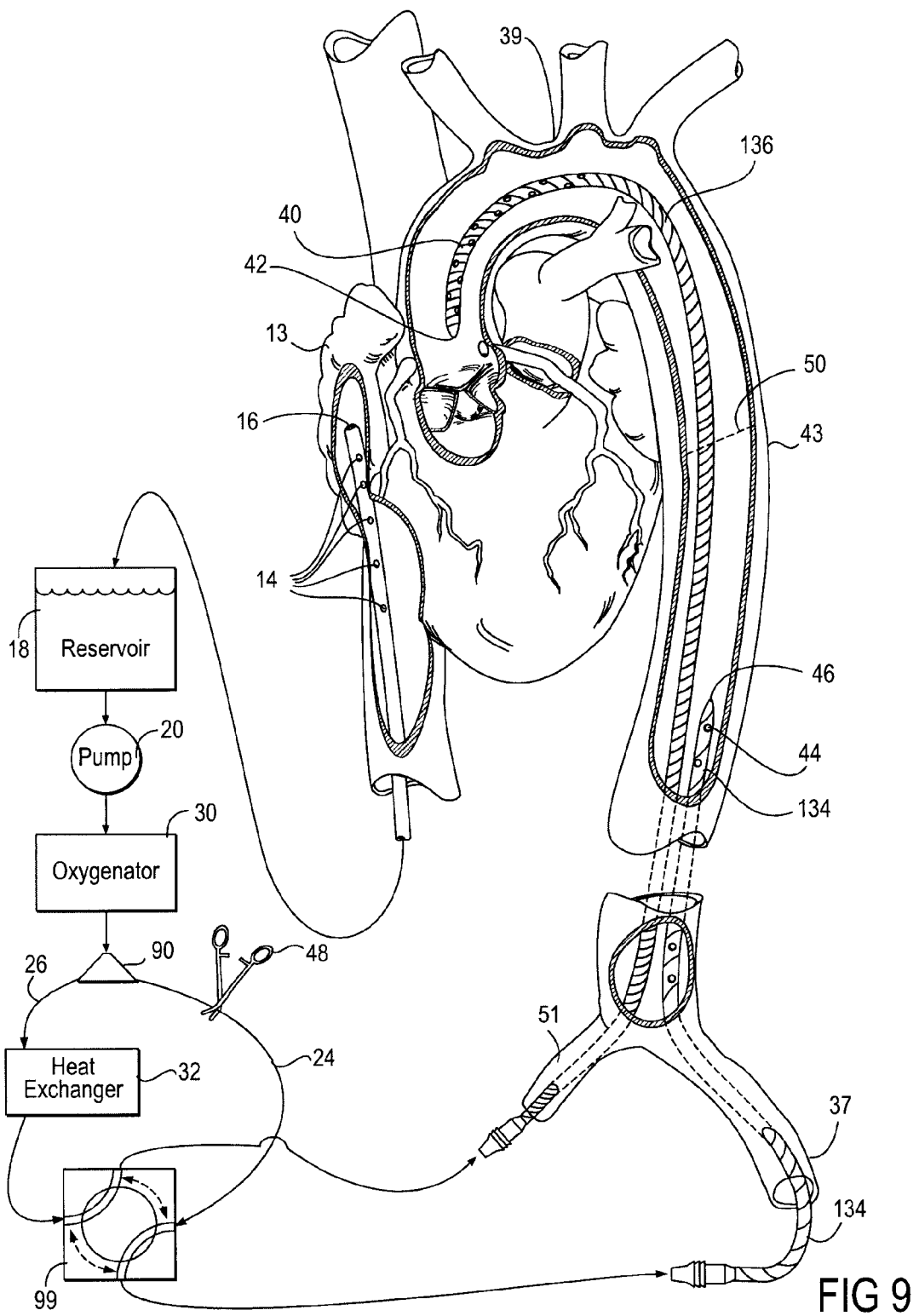
FIG. 9 is a semi-schematic illustration of a preferred embodiment configuration of the present invention wherein two single lumen perfusion catheters are introduced femorally and only one heat exchanger and oxygenator is employed.

FIG. 9. is a semi-schematic illustration of a ninth embodiment of the present invention wherein two single lumen perfusion catheters are employed to deliver differentially conditioned blood to the aorta. Blood is withdrawn from the venous reservoir 18 by a blood pump 20 and where tepid blood is directed to a membrane oxygenator 30 or other suitable oxygenating means. After oxygenation, the blood is separated into two separate flows 24, 26 by using an integral proportioning valve switch 90 which pre-proportions the blood flows to be delivered to the lumens of the catheters 134, 136. This embodiment is especially compact in that it uses only one heat exchanger 32 and one oxygenator 30. Any of a number of different conditioning devices can be called upon to condition one or both blood flows. An additional switching valve 99 is constructed to enable automatic switching of flow paths to the heat exchanger. The switch 99 as currently illustrated in FIG. 9 is in the cerebral position, meaning that fluid that has been conditioned by the heat exchanger is directed through the switch and to the cerebral circulation. By turning the switch counterclockwise, the switch 99 will be positioned in the corporeal position, meaning that fluid delivered through the heat exchanger will be directed to the corporeal circulation.

In this particular embodiment one perfusion catheter 134 is introduced through femoral artery 37 while the other perfusion catheter 136 is contralaterally introduced through the other femoral artery 51. The cerebral support catheter 136 through which the temperature adjusted blood flow is currently flowing is advanced in a retrograde direction so as to be positioned in the aortic arch 39. Perfusion ports 40 are formed near the distal end of the catheter to allow the escape of blood therefrom. An opening 42 formed in the distal end of the catheter facilitates its advancement into position along a guidewire. The corporeal support catheter 134 is advanced in a retrograde direction into position within the descending aorta 43. Perfusion ports 44 are formed near its distal end to allow the escape of blood therefrom. An opening 46 formed in the distal end of the catheter facilitates its advancement into position along a guidewire.

The cerebral support catheter 136 may be formed from a flexible thermoplastic material, a thermoplastic elastomer or a thermoset elastomer. More specifically, suitable materials for the cerebral support catheter 36 include, but are not limited to, PEBAX, PVC, PET, polystyrene, polyvinylchloride, polyurethane, polyethylene, polypropylene, polyamides (nylons), copolymers, polyesters, silicone, latex, and combinations thereof, as well as braided, coiled or counterwound wire reinforcement or filament reinforced composites. Alternatively, or in combination therewith, the cerebral support catheter 36 may be made of thin walled metallic tubing or hypotube, such as stainless steel, platinum, titanium, nitinol, alloys or Cobalt alloys such as Elgiloy and Carpenter MP 35.

The cerebral support catheter 136 has an outer diameter of about 5 to about 16 French and an inner diameter of approximately 0.053" to about 0.200" and has approximately one to twelve exit port(s) 40 formed therein, each approximately 0.039" to about 0.095" in diameter. The number of port(s) needed is correlative to the size of the ports as well as the lumen diameter and flow requirements. The combination of tubing diameter and port diameters must be able to yield a flow of approximately 0.5 L/min to about 2.0 L/min with about 5 mm Hg to about 200 mm Hg of pressure for the arch circulation. The catheter is preferably curved near its distal end to match the curvature of the aorta and is preferably reinforced with a helical winding of stainless steel wire or braided reinforcement. Such reinforcement should be spaced sufficiently apart in the location near the distal end of the catheter in order to accommodate the exit ports 40 residing therebetween. The corporeal support catheter 134 may similarly be formed of the same materials having an inner diameter and a sufficient number of holes to yield a flow of approximately three times that of the cerebral support catheter, i.e. approximately 1.5 L/min to about 6.0 L/min with about 25 mm Hg to about 200 mm Hg of pressure. The catheter may be similarly reinforced with a helical or braided coil of stainless steel wire.

Upon energization of pump 20, blood issues from the ports 40, 44 of both perfusion catheters 136, 134. By adjusting the relative flows through the two catheters, such as with the use of a clamp 48 to constrict one or both of the conduits 24, 26, or having preselection criteria from proportioning valve 90, so as to substantially match the flows to the requirements of the cerebral and corporeal subcirculation respectively, a state of equilibrium is achieved wherein the two flows remain separated by an inversion layer 50 that forms therebetween in the aorta. A cerebral to corporeal flow ratio of approximately 1:3 is required in order to reach a state of equilibrium whereby an inversion layer 50 is formed. An excessive flow rate issuing from the cerebral support catheter 136 will cause the superfluous volume to flow downwardly into the corporeal subcirculation. Conversely, an excessive flow rate issuing from the corporeal support catheter 134 will cause the superfluous volume to flow upwardly into the cerebral subcirculation. In certain applications, a slightly excessive cerebral flow rate may be desirable in order to ensure that an adequate supply of the blood conditioned for the cerebral subcirculation is actually delivered to the cerebral subcirculation, while any excess delivered into the corporeal subcirculation is quickly diluted by the substantially greater flow and volume associated with the corporeal vasculature.

While a particular form of the invention as been illustrated and described, it will also be apparent to those skilled in the art that various modifications can be made without departing from the spirit and scope of the invention. Accordingly, it is not intended that the invention be limited except by the appended claims.

What is claimed is:

1. A system for differentially perfusing selected subcirculation in a patient, comprising:
    a first lumen for delivering a first oxygenated blood flow to a first location in an artery;
    a second lumen for delivering a second oxygenated blood flow to a second location in said artery, downstream from said first location wherein said first and second blood flows are differentially conditioned; and
    means for controlling the relative flow rates through said lumens so as to cause an inversion layer to form in said artery between said first and said second location.

2. The differential perfusion system of claim 1, further comprising a third lumen for extracting blood from said patient for conditioning.

3. The differential perfusion system of claim 1, further comprising a single pump for communicating blood flow through said system.

4. The differential perfusion system of claim 2, further comprising a single heat exchanger operative to adjust the temperature of the extracted blood to be delivered by only one of said lumens.

5. The differential perfusion system of claim 1, wherein said first lumen has at least one perfusion port, said perfusion port is sized and said lumen is dimensioned to deliver a flow sufficient to support the cerebral subcirculation.

6. The differential perfusion system of claim 5, wherein said second lumen has at least one perfusion port and said port is sized and said lumen is dimensioned to deliver a flow sufficient to support the corporeal subcirculation.

7. The differential perfusion system of claim 6, wherein said first and second lumens are each disposed in separate catheters.

8. The differential perfusion system of claim 7, wherein said catheters are dimensioned for introduction via the femoral artery.

9. The differential perfusion system of claim 7, wherein said catheters are dimensioned for introduction via an aortotomy.

10. The differential perfusion system of claim 7, wherein said catheter having said first lumen disposed therein is dimensioned for placement via an aortotomy and said catheter having said second lumen disposed therein is dimensioned for placement via the femoral artery.

11. The differential perfusion system of claim 6, wherein said first and said second lumens are disposed in a single catheter and wherein said at least one perfusion port is in fluid communication with said first lumen and said at least one perfusion port in fluid communication with said second lumen are spaced relative to one another so as to facilitate their placement in the aortic arch and downstream of the left subclavian.

12. The differential perfusion system of claim 11, wherein said single catheter is dimensioned for placement via the femoral artery.

13. The differential perfusion system of claim 11, wherein said single catheter is dimensioned for placement via an aortotomy.

14. The differential perfusion system of claim 11, wherein said lumens are coaxially arranged within said catheter.

15. The differential perfusion system of claim 14, wherein said lumens are moveable within said catheter.

16. The differential perfusion system of claim 11, wherein said lumens are arranged in a side-by-side relationship within said catheter.

17. The differential perfusion system of claim 1, wherein the artery is the aorta.

18. A method for differentially perfusing preselected subcirculation within a patient, comprising the steps of:

delivering a first oxygenated blood flow to a first location in the aorta;

delivering a second oxygenated blood flow to a second location in the aorta, wherein said first and second blood flows are differentially conditioned; and controlling the relative flow rates through a fist and second lumen so as to cause an inversion layer to form between said first and second locations within the aorta.

19. The method of claim 18, wherein said first blood flow is controlled so as to match the requirements of the corporeal subcirculation.

20. The method of claim 18, wherein the first blood flow is delivered to the aortic arch and the second blood flow is delivered downstream of the left subclavian artery.

21. The method of claim 18, wherein said two blood flows are delivered through two separate catheters.

22. The method of claim 21, wherein said two catheters are introduced into the aorta via the femoral artery.

23. The method of claim 21, wherein said two catheters are introduced directly into the aorta through an aortotomy.

24. The method of claim 21, wherein one of said catheters is introduced into the aorta via the femoral artery and the other of said catheters is introduced directly into the aorta via a aortotomy.

25. The method of claim 18, wherein said two blood flows are delivered through two separate lumens contained in a single catheter.

26. The method of claim 25, wherein said catheter is introduced into the aorta via a femoral artery.

27. The method of claim 25, wherein said catheter is introduced directly into the aorta via an aortotomy.

28. The method of claim 18, wherein a single blood pump is employed to deliver said two blood flows.

29. The method of claim 25, wherein said two separate lumens are configured in a slidable relationship.

30. The method of claim 18, wherein said first blood flow is cooled to a temperature below said second blood flow.

31. The method of claim 18, further comprising alternating said first blood flow and said second blood flow through a heat exchanger.

32. The method of claim 31, wherein the step of alternating said blood flows is carried out by a switch.

* * * * *